United States Patent [19]

Aiman et al.

[11] Patent Number: 5,338,862
[45] Date of Patent: Aug. 16, 1994

[54] PROCESS FOR THE PRODUCTION OF 2-IMIDAZOLONES

[75] Inventors: Charles E. Aiman; Edward D. Daugs, both of Midland, Mich.

[73] Assignee: Merrell Dow Pharmaceuticals Inc., Cincinnati, Ohio

[21] Appl. No.: 39,539

[22] Filed: Mar. 29, 1993

Related U.S. Application Data

[63] Continuation of Ser. No. 971,713, Nov. 4, 1992, abandoned, which is a continuation of Ser. No. 902,437, Jun. 18, 1992, abandoned, which is a continuation of Ser. No. 818,510, Jan. 8, 1992, abandoned, which is a continuation of Ser. No. 751,596, Aug. 21, 1991, abandoned, which is a continuation of Ser. No. 639,392, Jan. 10, 1991, abandoned, which is a continuation of Ser. No. 511,870, Apr. 20, 1990, abandoned, which is a continuation of Ser. No. 379,730, Jul. 14, 1989, abandoned, which is a continuation of Ser. No. 181,015, Apr. 13, 1988, abandoned.

[51] Int. Cl.$^5$ ............................................. C07D 233/30
[52] U.S. Cl. ................................................... 578/316.4
[58] Field of Search ...................................... 548/316.4

[56] References Cited

PUBLICATIONS

O. Wong, et al., *Heterocycles*, 26(12), 3153–3158 (1987).
R. Duschinsky et al., *Journal of the American Chemical Society*, vol. 64, pp. 2350–2355 (1946).
Hoffman, Imidazole and Its Derivatives, Part I, Chapter III, p. 65, Interscience, New York (1953).
N. Leonard et al., *Journal of the American Chemical Socieity*, vol. 98, pp. 8218–8221 (1976).
W. Marckwald, *Berichte Deutschen Chem. Ges.* 25:2354–2373, 1892.

*Primary Examiner*—Robert W. Ramsuer
*Assistant Examiner*—Joseph K. McKane
*Attorney, Agent, or Firm*—Michael J. Sayles

[57] ABSTRACT

The present invention pertains to a process for producing a 2-imidazolone from a ureidoacetal. The ureidoacetal is subjected to an acid catalyzed condensation in order to produce the 2-imidazolone. The reaction is conducted in an alcoholic solvent in order to minimize the production of a polymeric by-product.

8 Claims, No Drawings

PROCESS FOR THE PRODUCTION OF 2-IMIDAZOLONES

This is a continuation of application Ser. No. 07/971,713, filed Nov. 4, 1992, now abandoned, which is a continuation of application Ser. No. 07/902,437, filed Jun. 18, 1992, now abandoned, which is a continuation of application Ser. No. 07/818,510, filed Jan. 8, 1992, now abandoned, which is a continuation of application Ser. No. 07/751,596, filed Aug. 21, 1991, now abandoned, which is a continuation of application Ser. No. 07/639,392, filed Jan. 10, 1991, now abandoned, which is a continuation of application Ser. No. 07/511,870, filed Apr. 20, 1990, now abandoned, which is a continuation of application Ser. No. 07/379,730, filed Jul. 14, 1989, now abandoned, which is a continuation of application Ser. No. 07/181,015, filed Apr. 13, 1988, now abandoned.

The present invention pertains to a process for the production of 2-imidazolones.

2-Imidazolones are useful as intermediates in the production of a large number of pharmaceutical compounds. For example, they are utilized in the production of biotin, as well as synthetic analogs of biotin. They are also utilized in the production of a class of cardiotonic agents which are described in U.S. Pat. No. 4,405,628.

In 1892 Marckwald, Bet., Vol. 25, page 2357, reported what was at the time believed to be a process for producing 2-imidazolones which can be described as follows:

a) reacting an isocyanate ion with an aminoacetal of the formula:

Formula I wherein R is represented by hydrogen or a $C_1$-$C_4$ alkyl, and each of $R_1$ and $R_2$ are independently represented by a $C_1$-$C_4$ alkyl; thereby producing an ureidoacetal of the formula:

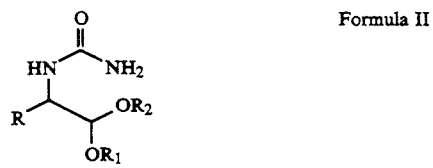

Formula II wherein R, $R_1$, and $R_2$ are as defined above, and;
b) subjecting the ureidoacetal produced above to an acid catalyzed condensation in order to produce a 2-imidazolone of the formula:

Formula III wherein R is as defined above.

In 1946 Duschinsky et al., Journal of the American Chemical Society, Vol. 64, page 2350, reported that the substance produced by this reaction sequence was not a 2-imidazolone. They reported that instead of forming a cyclic structure, the ureidoacetal undergoes an intramolecular condensation, with the resultant formation of a polymer rather than a 2-imidazolone. The authors also reported that this polymerization could be minimized by condensing the ureidoacetal in a dilute solution at room temperature.

Conducting the condensation at room temperature and in dilute concentrations renders this procedure impractical for large scale industrial synthesis. The volume of material which must be handled dramatically increases the costs of the imidazolones produced thereby and also increases the difficulty of recovering the imidazolone from the reaction medium. The reaction is relatively slow at room temperature which further increases costs.

Thus, it would be a valuable contribution to the art to develop a procedure wherein the ureidoacetal could be converted into a 2-imidazolone, of Formula III at elevated temperatures and in the presence of high concentrations of the ureidoacetal.

In accordance with the present invention, it has been discovered that when the acid catalyzed condensation of the ureidoacetal is conducted in the presence of an alcoholic solvent, the reaction can be run at elevated temperatures and in the presence of high concentrations of the ureidoacetal without producing excessive quantities of the intramolecular polymer described above.

In this application, the term elevated temperatures refers to a temperature range of from about 50° C. to about 100° C. Also in this application, the phrase "in the presence of high concentrations of ureidoacetal", refers to a concentration range of from about 5 grams to about 30 grams of ureidoacetal per 100 grams of solvent.

The aminoacetal starting material of Formula I should correspond structurally to its counterpart in the desired 2-imidazolone. Thus, for example, if the desired 2-imidazolone is substituted with a methyl function at the 4-position, then R in the aminoacetal which is utilized should also be represented by a methyl radical.

Some of the aminoacetals of Formula I are available commercially. Those not available commercially can be prepared by methods known in the art. One such method entails carrying out a reductive amination upon a ketoacetal of the formula:

Formula IV wherein R, $R_1$, and $R_2$ are as defined above. The particular keto-acetal utilized should correspond structurally to the desired aminoacetal For example, if R, $R_1$, and $R_2$ are (methyl in the desired aminoacetal, then R, $R_1$, and $R_2$ should also be methyl in the keto-acetal which is utilized.

The reductive amination can be conducted according to techniques which are known in the art. Typically, the reduction is carried out in the presence of ammonia and hydrogen, utilizing a reducing catalyst such as nickel, palladium or platinum. The reduction is typically carried out at a temperature range of from 50°–120° C. for a period of time ranging from 0.5–12 hours.

Regardless of how the aminoacetal is obtained, the first step in the overall synthetic procedure is to react the aminoacetal with an isocyanate ion, in order to produce a ureidoacetal as described by formula II. The particular cation that is associated with the isocyanate ion is not critical to the present invention. Suitable cations include sodium, potassium or ammonium. Generally the isocyanate ion will be present in a quantity of from 1–3 moles for every mole of aminoacetal which is present, and more preferably the isocyanate ion is present in the quantity of from 1.1–2 moles.

The reaction is also typically conducted in the presence of a mineral acid. Suitable mineral acids include hydrochloric, hydrobromic, sulfuric, hydrofluoric, and phosphoric. The mineral acid will typically be present in the reaction zone in a quantity of from about 0.95 moles to about 1.1 moles for every mole of aminoacetal present in the reaction zone. The reaction zone is typically cooled to a temperature below 10° C. while the acid is initially added to the reaction zone. After the addition is completed, cooling can be discontinued.

It is preferred that the reaction be conducted at a temperature range of from about 20° C. to about 50° C. It is also be preferred that the reaction be conducted in a solvent such as water.

After the reaction is completed, the water should be removed from the reaction medium prior to the next step in the reaction, (i.e. the acid catalyzed condensation of the ureidoacetal). The presence of water promotes the formation of the undesired polymer by-product and thus should be removed.

The water can be removed by numerous techniques known to those skilled in the art. A currently preferred manner is to remove most of the water by vacuum distillation. An appropriate volume of an alcoholic solvent, such as 2-propanol, is then added to the reaction medium, and any remaining water is removed via an azeotropic distillation. Finally the reaction medium is dried with magnesium sulfate. Alternative methods of removing the water include separating the ureidoacetal from the reaction medium by either concentration or extraction, crystallizing the ureidoacetal from a solvent system such as ethyl acetate, and oven drying the resulting product.

The next step in the synthesis is to subject the ureidoacetal of Formula II formed in the previous step, to an acid catalyzed condensation, thereby forming the desired 2-imidazolone of Formula III.

The particular ureidoacetal utilized should correspond structurally to the desired 2-imidazolone. For example, if R in the desired 2-imidazolone is methyl, then R in the ureidoacetal which is utilized, should also be represented by a methyl group.

The acid catalyzed condensation can be conducted with a variety of acids. Representative examples of suitable acids include hydrochloric, hydrobromic, hydrofluoric, phosphoric, sulfuric, methane sulfonic, acetic, and ammonium chloride. As noted above, the presence of water increases the amount of polymer which is formed. Therefore, it is preferred that the acid which is utilized be anhydrous. It is currently preferred that the acid be present in the reaction zone in a quantity of from about 5 to about 20 mole % based upon the quantity of ureidoacetal present.

Alternatively, the condensation can be catalyzed with an acidic ion exchange resin. These resins typically are composed of a plastic backbone to which is attached a protonated anion. These resins are known in the art, as well as methods of carrying out analogous condensation reactions.

In order to minimize the quantity of polymer which is formed, the reaction is conducted in an alcoholic solvent. Suitable alcohols include methanol, ethanol, propanol, isopropanol, n-butanol, sec-butanol, and tert-butanol.

As discussed above, the alcoholic solvent allows the reaction to be conducted at elevated temperatures. Typically, the reaction will be conducted at a temperature range of from about 50° C. to about 100° C., and more preferably from about 75° C.–85° C. Typically the reaction is carried out for a period of time ranging from about ½ hour to about 20 hours and more preferably from about 2 hours to about 6 hours.

The alcoholic solvent also allows the reaction to be conducted utilizing concentrations of ureidoacetal far greater than the method of the prior art. Generally, the ureidoacetal can be present in the reaction zone in a quantity of from about 5 grams to about 30 grams for every 100 grams of solvent utilized, and more preferably the ureidoacetal is present in the quantity of from about 15 grams to about 20 grams.

The 2-imidazolone can be recovered from the reaction zone by numerous techniques known to those skilled in the art. One such suitable technique is a solvent exchange utilizing 2-propanol and ethyl acetate. Other suitable solvent systems include butanol/ethyl acetate, ethanol/ethyl acetate, and methanol/ethyl acetate.

The following examples are presented in order to further illustrate the present invention. They should not be construed as limiting the invention in any manner.

EXAMPLE I

The purpose of this example is to demonstrate one manner of preparing an aminoacetal from a keto-acetal.

To a 600 ml stainless steel Parr reactor was added 3.0 g of Hatshaw Nickel on alumina catalyst, 300 ml of methanol, and 63.0 g (0.534 mole) of pyruvic aldehyde dimethyl acetal. The reactor was sealed, then charged with 31 g (1.82 mole) of anhydrous ammonia, resulting in a temperature increase of from 25° to 57° C. The reactor was pressurized to 150 psi with hydrogen, then heated at 75° C. for 12 hours. After cooling, the catalyst was removed by filtration through Celite, and the solution concentrated on a rotary evaporator. The residue (110 g) was distilled at 90 mmHg, collecting the 70° to 80° C. fraction to give 53.96 g (0.453 mole, 85% yield) of 2-aminopropanal dimethyl acetal.

EXAMPLE II

The purpose of this example is to demonstrate: 1) the formation of a ureidoacetal from the reaction between an aminoacetal and an isocyanate ion, and 2) the formation of a 2-imidazolone from the acid catalyzed condensation of a ureidoacetal which has been carried out in an alcoholic solvent.

In a 500 ml round bottom flask, 42.14 g (0.354 mole) of 2-aminopropanal dimethyl acetal in 125 ml of water was cooled to 5° C., and 35.25 g (0.358 mole) of 37% aqueous hydrochloric acid was added dropwise with stirring, maintaining the temperature below 10° C. In a separate flask, 30.15 g (0.372 mole) of potassium isocyanate was dissolved in 50 ml of water, and this solution added dropwise to the solution of 2-aminopropanal dimethyl acetal.HCl. The mixture was warmed to 40°–50° C. for 3 hours. Progress of the reaction was monitored by TLC (20% methanol in chloroform). After completion, the major portion of water was removed by vacuum distillation thereby producing a solid white residue, (119 g) containing 2-ureidopropanal dimethyl acetal and inorganic salts. 300 ml of 2-propanol was then added, and the remaining water was removed by azeotropic distillation using anhydrous magnesium sulfate in a Soxlet extractor.

Anhydrous hydrogen chloride in ethanol (14 g of a 7.7 wt % solution, 0.03 mole HCl) was then added to the fraction containing the ureidoacetal, and the mixture was heated at reflux for 2 hours. Progress of the reaction was monitored by TLC (20% methanol in chloroform). After completion, 10 g each of sodium carbonate and sodium bicarbonate were added, the white slurry was heated at reflux for 30 minutes, then filtered while hot. The solvent was evaporated by vacuum distillation to produce a solid residue (60 g). 25 ml of 2-propanol was then added and the slurry heated to reflux, triturated with 75 ml of ethyl acetate, then cooled to 10° C., filtered, washed with ethyl acetate, and dried at 60° C. under vacuum to give 26.49 g (0.257 mole, 72% yield) of 1,3-dihydro-4-methyl-2-H-imidazol-2-one.

EXAMPLE III

The purpose of this example is to demonstrate the results obtained when the acid catalyzed condensation is conducted using a hydrous mineral acid, rather than an anhydrous acid.

A solution of 7.55 g ($4.66 \times 10^{-2}$ mole) of 2-ureidopropanal dimethyl acetal and 0.25 ml ($3 \times 10^{-3}$ mole) of 37% aqueous hydrochloric acid in 50 ml of ethanol was heated at reflux for 19 hours, then cooled to 20° C. and neutralized with 0.25 g ($3 \times 10^{-3}$ mole) of sodium bicarbonate. The solvent was removed by vacuum distillation to give a 7.5 g solid residue. Recrystallization from 12 ml of water afforded, after drying at 60° C. under vacuum, 2.17 g of 1,3-dihydro-4-methyl-2H-imidazol-2-one ($2.07 \times 10^{-2}$ mole, 44% yield).

EXAMPLE IV

The purpose of this example is to demonstrate the acid catalyzed condensation utilizing an acidic ion exchange resin, rather than a mineral acid.

To 14.7 g ($9.07 \times 10^{-2}$ mole) of 2-ureidopropanal dimethyl acetal in 60 ml of ethanol was added 2.0 g of DOWEX® MSC1-H ion exchange resin, and the mixture was heated at reflux for 14 hours, then cooled to 20° C. The ethanol solution was decanted from the resin and the solvent removed by vacuum distillation on a rotary evaporator to give 11 g of solid residue. Recrystallization from 20 ml of water afforded 3.92 g of 1,3-dihydro-4-methyl-2H-imidazol-2-one ($3.84 \times 10^{-2}$ mole, 42% yield).

EXAMPLE V

The purpose of this example is to demonstrate another method for the preparation of a ureidoacetal.

In a 250 ml flask, 20.18 g (0.170 mole) of 2-aminopropanal dimethyl acetal in 60 ml of water was cooled to 5° C., then 16 7 g (0 170 mole) of 37% aqueous hydrochloric acid was added dropwise at a rate to maintain the temperature below 10° C. In a separate flask, 16.5 g (0.203 mole) of potassium cyanate was dissolved in 25 ml of water, then added to the amine hydrochloride solution, and the mixture warmed to 30° to 60° C. for 2 hours. After cooling to 20° C., the aqueous solution was placed in a liquid/liquid extractor and extracted with 200 ml of ethyl acetate for 22 hours. The ethyl acetate solution was cooled to 5° C. and the precipitate collected to give, after drying at 60° C. under vacuum, 22.17 g (0.137 mole, 80% yield) of 2 -ureidopropanal dimethyl acetal (mp 102°-103° C.).

What is claimed is:

1. A process for producing a 2-Imidazolone of the formula:

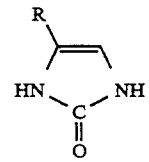

wherein R is represented by hydrogen or a $C_{1-4}$ alkyl, comprising conducting an acid catalyzed condensation, in an alcoholic solvent, at about 50° C. to about 100° C. ureidoacetal of the formula:

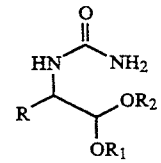

wherein R is represented by hydrogen or a $C_{1-4}$ alkyl, and each of $R_1$ and $R_2$ are independently represented by a $C_{1-4}$ alkyl.

2. The process of claim 1, wherein said acid catalyzed condensation is conducted with an anhydrous acid.

3. The process of claim 2, wherein said acid is selected from the group consisting of hydrochloric, hydrobromic, hydrofluoric, phosphoric, and sulfuric, methanesulfonic, and ammonium chloride.

4. The process of claim 2, wherein said acid condensation is conducted with an acidic ion exchange resin.

5. The process of claim 1, wherein said alcoholic solvent is selected from the group consisting of methanol, ethanol, propanol, isopropanol, n-butanol, sec-butanol, and tert-butanol.

6. The process of claim 1, wherein said 2-imidazolone is 1,3-Dihydro-4-methyl-2-H-imidazol-2-one.

7. The process of claim 6 wherein said alcohol is isopropanol and said mineral acid is anhydrous hydrogen chloride.

8. The process of claim 1, wherein said ureidoacetal is produced by reacting an aminoacetal of the formula:

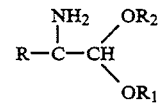

wherein R, $R_1$, and $R_2$ are as defined above, with an isocyanate ion, in the presence of a mineral acid.

* * * * *